US011300558B2

(12) United States Patent
Uplinger, II et al.

(10) Patent No.: US 11,300,558 B2
(45) Date of Patent: Apr. 12, 2022

(54) APPARATUS AND SYSTEM FOR SPECTROSCOPY AND TOMOGRAPHY OF FRAGILE BIOLOGIC MATERIALS

(71) Applicant: Nokomis, Inc., Charleroi, PA (US)

(72) Inventors: James Robert Uplinger, II, Cranberry Township, PA (US); Vladimir Makarenko, McDonald, PA (US)

(73) Assignee: NOKOMIS, INC., Canonsburg, PA (US)

( * ) Notice: Subject to any disclaimer, the term of this patent is extended or adjusted under 35 U.S.C. 154(b) by 542 days.

(21) Appl. No.: 16/008,501

(22) Filed: Jun. 14, 2018

(65) Prior Publication Data

US 2019/0383787 A1 Dec. 19, 2019

(51) Int. Cl.
*G01N 33/483* (2006.01)
*G01N 27/22* (2006.01)
*C12M 1/34* (2006.01)
*G06N 3/08* (2006.01)
*G01S 13/89* (2006.01)
*G01N 22/00* (2006.01)

(52) U.S. Cl.
CPC ......... *G01N 33/4833* (2013.01); *C12M 41/36* (2013.01); *G01N 27/221* (2013.01); *G06N 3/084* (2013.01); *G01N 22/00* (2013.01); *G01S 13/89* (2013.01)

(58) Field of Classification Search
CPC ........ G01N 22/00; G01N 22/02; G01N 27/02; G01N 27/023; G01N 27/025; G01N 27/026; G01N 27/221; G01N 33/4833; G01N 2223/03; G01N 2223/052; G01N 2223/615; G01N 33/4836; G01N 33/48707; G01N 33/48721; G01N 33/48728; G01N 33/48735; G06N 3/084; G01S 13/89; C12M 41/36
USPC .......................................................... 324/663
See application file for complete search history.

(56) References Cited

U.S. PATENT DOCUMENTS

| | | | | |
|---|---|---|---|---|
| 5,130,661 A * | 7/1992 | Beck | ..................... | G01N 27/226 324/663 |
| 5,715,819 A * | 2/1998 | Svenson | ................... | A61B 5/05 600/425 |
| 6,387,671 B1 * | 5/2002 | Rubinsky | .............. | A61B 5/0536 435/173.1 |
| 6,403,348 B1 * | 6/2002 | Rubinsky | ................ | C12M 35/02 435/173.1 |
| 6,482,619 B1 * | 11/2002 | Rubinsky | ................ | C12M 35/02 435/173.1 |
| 6,885,191 B1 * | 4/2005 | Gleman | .................... | A61B 5/05 324/300 |
| 7,119,553 B2 * | 10/2006 | Yang | ....................... | G01R 27/00 324/663 |
| 7,295,019 B2 * | 11/2007 | Yang | ....................... | G01R 27/00 324/663 |
| 7,312,742 B2 * | 12/2007 | Steinway | .............. | G01S 13/878 342/128 |

(Continued)

*Primary Examiner* — Steven L Yeninas
(74) *Attorney, Agent, or Firm* — AP Patents; Alexander Pokot (57) ABSTRACT

An apparatus and system to nondestructively analyze 2D and 3D cell cultures for cell health using a combination of RF spectroscopy and a radio tomography. The apparatus acquires a signal using a low noise, highly sensitive detector. The signals are combined and compared to the signal of healthy cells.

15 Claims, 7 Drawing Sheets

(56) References Cited

U.S. PATENT DOCUMENTS

| | | | |
|---|---|---|---|
| 7,496,450 B2* | 2/2009 | Ortiz Aleman | G01F 1/64 702/6 |
| 7,671,784 B2* | 3/2010 | Steinway | G01S 13/86 342/22 |
| 8,762,084 B2* | 6/2014 | Gao | G01N 27/228 702/65 |
| 9,933,380 B2* | 4/2018 | Fouchard | G01N 27/026 |
| 10,041,899 B2* | 8/2018 | Deabes | G01N 27/221 |
| 10,197,508 B2* | 2/2019 | LoVetri | A61B 5/0507 |
| 10,551,339 B2* | 2/2020 | Marashdeh | G01F 1/64 |
| 11,083,393 B2* | 8/2021 | Loh | A61B 5/0531 |
| 2001/0051774 A1* | 12/2001 | Littrup | A61B 5/4312 600/547 |
| 2002/0137121 A1* | 9/2002 | Rubinsky | G01N 33/5014 435/29 |
| 2009/0039900 A1* | 2/2009 | Podhajsky | G01N 27/221 324/663 |
| 2011/0109328 A1* | 5/2011 | Gulbranson | G01N 27/221 324/664 |
| 2013/0214797 A1* | 8/2013 | Gruden | G01N 27/221 324/663 |
| 2014/0182362 A1* | 7/2014 | Potyrailo | G01N 27/026 73/64.53 |
| 2014/0218230 A1* | 8/2014 | Ostadrahimi | G01N 22/00 342/179 |
| 2015/0097579 A1* | 4/2015 | Sharma | G01N 22/00 324/637 |
| 2015/0168313 A1* | 6/2015 | Jean | G01N 22/00 324/639 |
| 2015/0338364 A1* | 11/2015 | Fan | A61B 5/0536 324/663 |
| 2016/0091448 A1* | 3/2016 | Soleimani | G01N 27/22 324/654 |
| 2016/0377557 A1* | 12/2016 | Kimura | G01N 22/00 324/638 |
| 2017/0156646 A1* | 6/2017 | Gulati | A61B 5/14546 |
| 2017/0188874 A1* | 7/2017 | Suhami | A61B 5/4547 |
| 2018/0074103 A1* | 3/2018 | Safavi-Naeini | G01N 22/00 |
| 2018/0206760 A1* | 7/2018 | Rubinsky | A61B 5/7228 |
| 2018/0313969 A1* | 11/2018 | Mirisharif | G01N 27/221 |
| 2018/0325414 A1* | 11/2018 | Marashdeh | A61B 5/0536 |
| 2019/0170677 A1* | 6/2019 | Bianchi | G01N 27/221 |
| 2019/0266436 A1* | 8/2019 | Prakash | G06N 3/0481 |
| 2019/0285562 A1* | 9/2019 | Penny | G01N 27/045 |
| 2019/0317026 A1* | 10/2019 | Hu | G01N 22/02 |
| 2020/0003670 A1* | 1/2020 | Hunt | G01F 1/64 |

* cited by examiner

APPARATUS AND SYSTEM FOR SPECTROSCOPY AND TOMOGRAPHY OF FRAGILE BIOLOGIC MATERIALS

FEDERALLY SPONSORED RESEARCH OR DEVELOPMENT

N/A

REFERENCE TO SEQUENCE LISTING, A TABLE, OR A COMPUTER PROGRAM LISTING COMPACT DISC APPENDIX

N/A

BACKGROUND OF INVENTION

Use of radio frequency (RF) to characterize of cell cultures presents a problem of measuring biologic materials nondestructively because the exposure of cultures at sufficient energy to perform spectroscopy or tomography causes degradation of the cells or other fragile biologic material such as proteins.

Biopharmaceutical process characterization focuses on parameters such as cell growth, yield, product quality, temperature, pH, $pO_2$, $pCO_2$, and metabolite levels. Biological systems are very sensitive to process changes, resulting in unviable bioproducts. Current manual measurement techniques are inadequate to provide accurate real-time automated viability testing, by either being limited by image analysis or involving destructive testing of the culture, by complex microfluidic chambers to isolate small samples of the specimen, or by the inability to non-destructively probe three-dimensional cell cultures. Adequate monitoring of cell cultures is needed in testing specificity and response time to provide the needed relative cellular health feedback that will be used to increase quality and decrease in production time and costs. Expensive carefully prepared cell lines may be lost due to the delays incurred in testing and performance mitigating responsive actions.

The better known transmission tomographic images are generally formed by illuminating an object with x-rays or microwaves and measuring the energy that passes in a straight ray propagation, the measurement can be the amplitude or the time of arrival of the received signal; with reflection tomography, the reflected, and refracted signal can be measured. The use of penetrating RF signals, and the reconstruction of the signals after passing through targets of interest to identify subsurface features has been proven a successful technique for biomedical imaging applications, such as Computed tomography (CT) of the heart, abdomen, and pelvis, as well as MRI. These tomographic images are formed by illuminating an object with energy such as x-rays, microwaves, or ultrasound; and measuring the energy that passes straight ray propagation. The antennas are typically arranged to surround the target with transmitting antenna moving through a circle.

Currently, the use of dielectric or reflective RF tomography has been limited to determining the presence or amount of biomass. At power levels currently used these applications are destructive, damaging cells, tissues, or other biologic materials such as proteins.

BRIEF SUMMARY OF INVENTION

To address the need for real time monitoring of 2 dimensional (2D) and 3 dimensional (3D) cellular cultures, a combined radio frequency capacitive and reflective tomography device is used to monitor for tissue viability and purity. Cellular properties strongly influence their dielectric properties, across the vast range of DC to RF and millimeter wave frequencies. By monitoring both the dielectric response versus frequency in the near field, as well as measuring the far field propagation and reflection across an ultra-wide bandwidth, the overall cellular health can be rapidly and non-invasively measured. The use of a variety of capacitive sensors, a far field antenna array, and an embedded analysis system for rapid analysis feedback of the condition of the sample. These systems will require minimal training and can be used by ordinary users.

The proposed technology will also provide the identification of contamination through identification of other cells and debris from their different dielectric responses, as well as the cell viability. Physical properties of samples change as their its relative health degrades.

The device uses highly sensitive RF detectors characterizing biomaterial, chemical species, and RF spectroscopy. The increase in sensitivity of RF sensors allows for non-destructive cellular culture and biologic material analysis for real time measurements of cell health and viability.

In order to perform real time monitoring of 2D and 3D cellular samples a device combining radio frequency capacitive and tomography device to monitor for tissue viability and purity is described. Cellular properties strongly influence their dielectric properties, across the range of DC to RF and millimeter wave frequencies, and by monitoring both the dielectric response versus frequency in the near field, as well as measuring the far field propagation and reflection across an ultra-wide bandwidth, overall culture health can be rapidly and non-invasively measured. One embodiment of a standalone device and system that receives biomass samples. Another embodiment is configured to measure larger 3D cell cultures in special conditions. The device has a variety of capacitive sensors, a far field antenna array, and an embedded analysis system for rapid analysis feedback. These systems will require minimal training and can be used by low tech users.

The described technology will also provide the identification of contamination through identification of other cells and debris from differences in its dielectric responses compared to the targeted biological sample, as well as the cell viability as the physical properties of the cells change as their relative health degrades. A sensitive Radio Frequency (RF) sensor system, such as the Nokomis Hiawatha™ will be used to collect electromagnetic emissions and responses, convert the signals into the frequency domain, and perform spectral analysis. This technology offers extensive capability and sensitivity in RF sensing of chemical species, biomaterial characterization, and RF spectroscopy. The described technology provides a reliable, non-destructive cellular culture analytical device for real time measurements of cell health and viability.

DETAILED DESCRIPTION OF INVENTION

Dielectric Spectroscopy

Dielectric spectroscopy is a near field measurement technique that is based on the passive electrical properties of a material, the capacitance C, and the conductance G. The sample is placed between two electrodes with an oscillating electric field; the material properties of the sample between the two electrodes respond with the changing field to amplify or attenuate the signal depending of the frequency of oscillation. The relative permittivity et and conductivity k describe the relation independent from the electrodes given by the following equations:

$$C = \varepsilon_T \varepsilon_0 \left(\frac{A}{d}\right)$$

$$G = \kappa \left(\frac{A}{d}\right)$$

These apply for parallel plate electrodes with a surface area A with a separation d. Specifically, for a suspension of ideal spherical cells with radius r and the capacitance per membrane unit are $C_m$, the capacitance is:

$$C = \frac{9rPC_m d}{4A}$$

Where P is the volume fraction of the cells in the suspension volume between the parallel plate electrodes, and the cell volume is given as $4/3\pi r^3$. With a cell density per unit volume N the capacitance can be made a function of the cell radius and correlates linearly with the cell density per membrane unit area:

$$C = \frac{3\pi r^4 NC_m d}{A}$$

Figure 1:
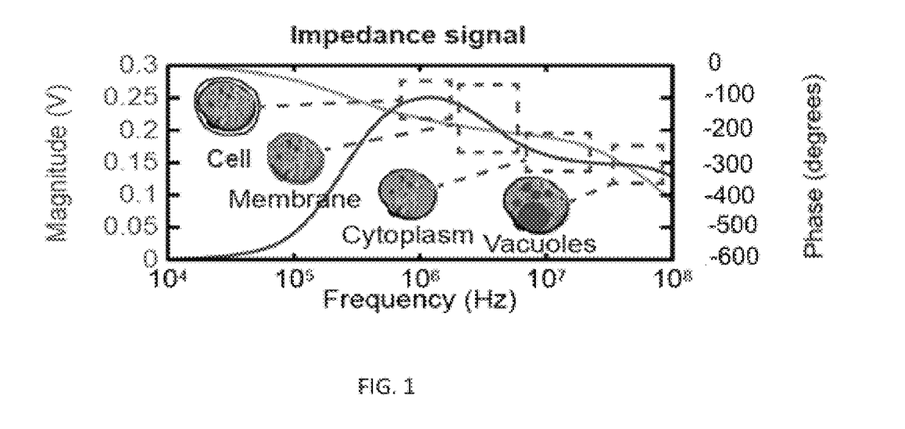
FIG. 1 is an illustration of the dielectric response as a function of frequency and various biologic matter.
Figure 2:
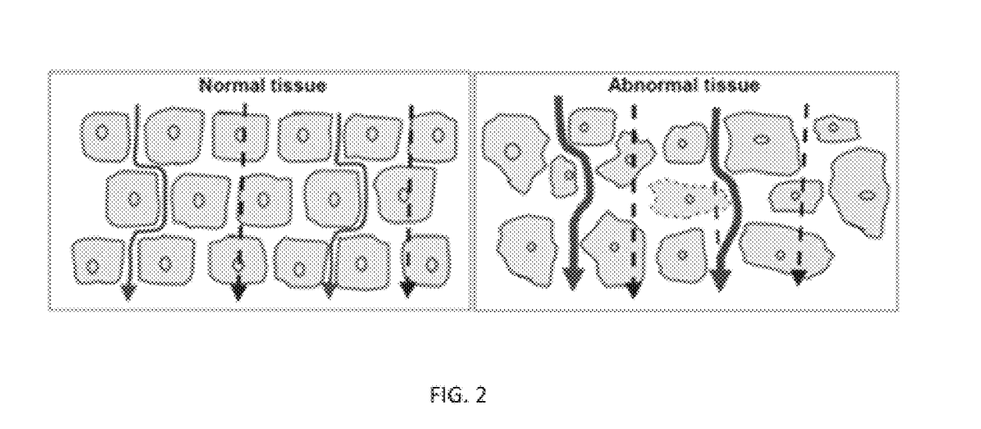
FIG. 2 is an illustration of the current path through a sample of normal and abnormal tissue in dielectric spectroscopy.

Using these fundamentals, tissue health can be identified using these principles. FIG. 1 illustrates the impedance and phase response across frequencies for various cellular properties. FIG. 2 illustrates the current flow between cells comparing normal and abnormal tissue.

The solid lines correspond to the current flow due to low frequency signals, while the dashed lines correspond to current paths at higher frequency signals. At higher frequencies the current is able to permeate cell membranes, which effectively probe their physical properties. Low frequencies do not permeate the cell membranes due to the polarized nature of cells. At low frequencies the cells are able to rotate and align with the fields. At higher frequencies the RF field is able to permeate the cell membrane and allows for measurements inside the cell. For bulk cellular cultures physical properties of the sample will change as the cells become unviable or deviate from the intended bioproduct. In FIG. 2 abnormal cells are illustrated. As cell membranes start to break down the low frequency signals will start to have paths that pass through the cells themselves, leading to a range of significantly different impedance values.

Near field dielectric spectroscopy measurements can be performed on both 2D and 3D cell cultures. First, broadband RF spectral data is acquired. Broadband data is collected with the intact cell culture. Wide band spectral measurements will be collected with frequencies ranging from 1 MHz to 1000 MHz to cover the range of measurements relevant to cellular environments. These parameters including: biomass, cell size, intracellular matrix, cellular membrane health, subcellular matrix properties.

Potential harm can come to cell cultures, particularly 3D cultures, if the cells try to align with the electric fields. The dielectric spectroscopy measurements described will utilize very low power, typically less than 10 mW. The ability to use low power for these measurements is enabled by use a very sensitive Radio Frequency (RF) sensor system, such as the Nokomis Hiawatha™, capable of sensitivities of −170 dB.

Radio Tomography

An advantage to using reflective tomography is that it can operate at a lower emission power in that it is not necessary to completely penetrate the target sample.

In reflective tomography, unlike transmission tomography, the antenna or antennas are arranged to receive the reflections. Where more than one receiving antenna is used one embodiment is a generally linear alignment of the antennae. Another embodiment is to arrange the antennae in a generally semicircular fashion.

Figure 3:
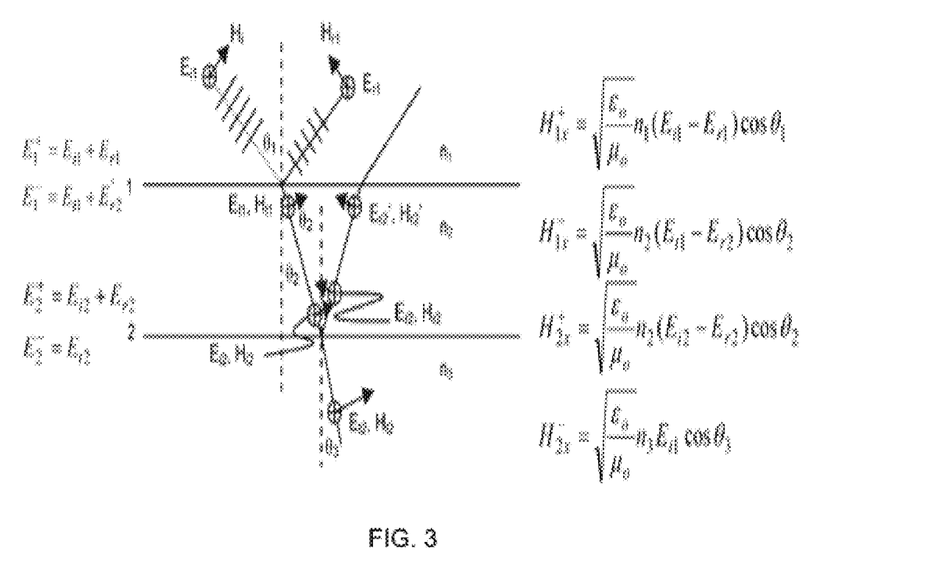
FIG. 3 is an illustration of reflection, refraction and of RF emission by a multi layered sample in reflective tomography.

The signals reflect, refract, and deflect at specific angles, dependent on the material properties at each interface. See FIG. 3. As the signals pass through, the phase and polarization can change and provide information about the interior structure of the material and detect boundaries between different materials. Often, many receiver antennas are used to calculate difference in multiple directions, to give an advanced image of interfaces of the materials.

The RF tomography approach, utilizing 1-40 GHz, will enable property measurements at all levels of the culture, layer by layer.

Combined Radio Tomography and Dielectric Spectroscopy

Figure 4:
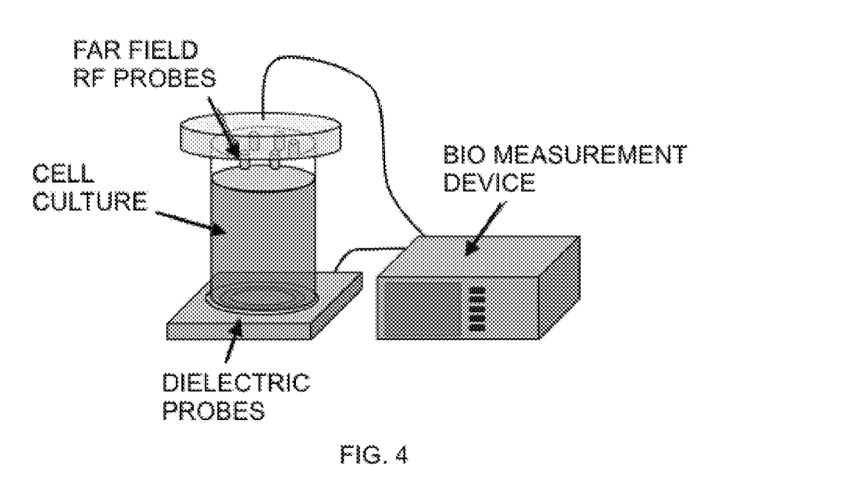
FIG. 4 is a is a perspective view of an embodiment of the apparatus connected to a bioproperty measuring device.

A perspective view of a resonant cell is shown in FIG. 4. In this preferred embodiment, the cell and its connection to a biomaterial identification device is shown. The radio tomography probes, antennas, are shown inside the cell with the dielectric probe shown on the bottom, outside of the cell.

Figure 5:
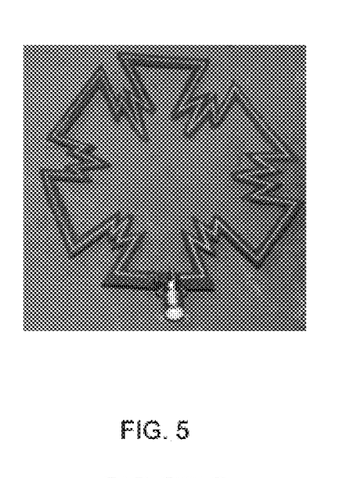
FIG. 5 plan view of an embodiment of a semi-fractal antenna.

FIG. 5 is a plan view showing a semi-fractal antenna.

Figure 6:
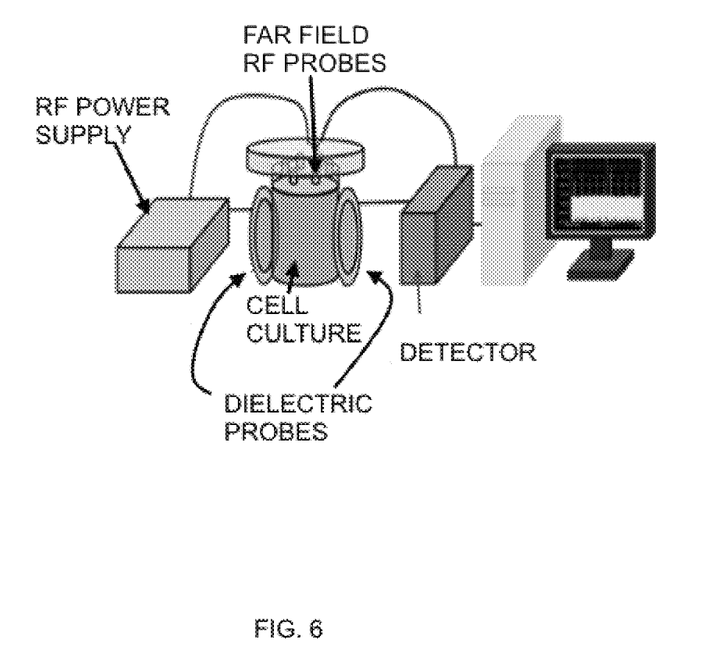
FIG. 6 is a perspective view of another embodiment of the apparatus connected to an RF Power supply, sensitive detector and controller with a polygonal antenna array.

FIG. 6 Is an embodiment with the cell connected to an RF power supply connected to the cell and the probes; the dielectric and far field probes are connected to a sensitive detector 600 and computer controller 630. In this embodiment the far field RF probes/antennas are in a polygonal patter and the near field dielectric antenna/probes are positioned on the side of the resonant cell.

Figure 7:
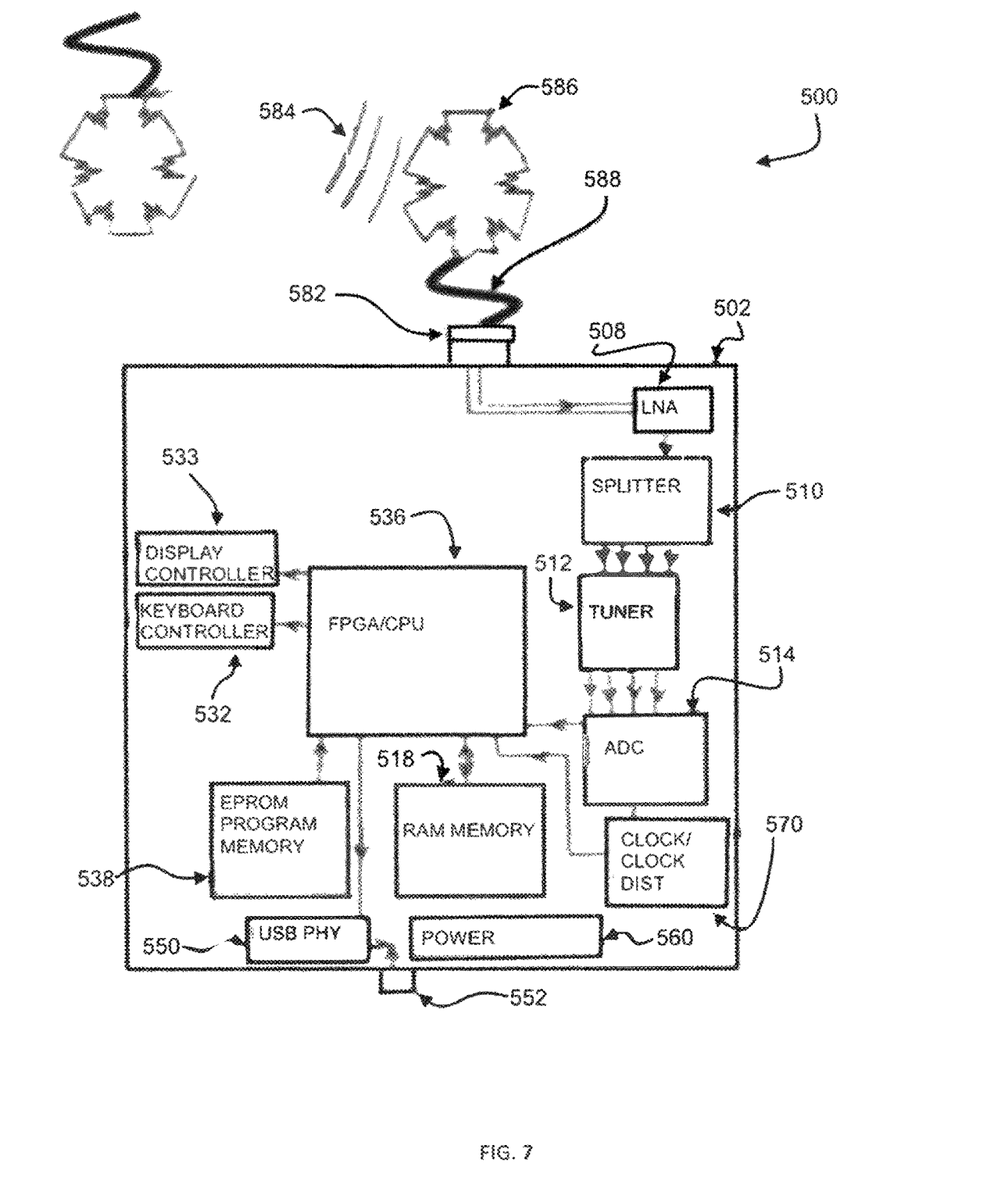
FIG. 7 a block diagram of a sensitive detector.

FIG. 7 shows a block diagram of the antennas 586, sensitive detector 500 connected to the analysis circuits 630. The sensitive detector 500 has an input from antenna 586 through cable 588 at input port 582. The sensitive detector 600 acquires the signal 584. The signal 584 is received by a Low Noise Amplifier 508 and is divided by a splitter 510. A tuner 512 receives the signal from the splitter 510 and is converted by an Analog to Digital Converter (ADC) 514.

A sensitive detector preferably has a sensitivity of −170 dB at room temperature, 4 dB higher than the theoretical limit. A standard range is between 30 MHz to 1000 MHz, but the detector is not limited to this range and can be modified by replacing the tuning system for different frequency range. A FPGA/CPU 556 receives the signal from the ADC 514 and preferably, a clock 570. The FPGA has a display controller 510 and a keyboard controller 512. The FPGA communicates with RAM memory 518 and preferably an EPROM 538. The FPGA outputs to USB physical layer 550 at output port 552. The unit 500 has an internal and/or external power supply 560.

Figure 8:
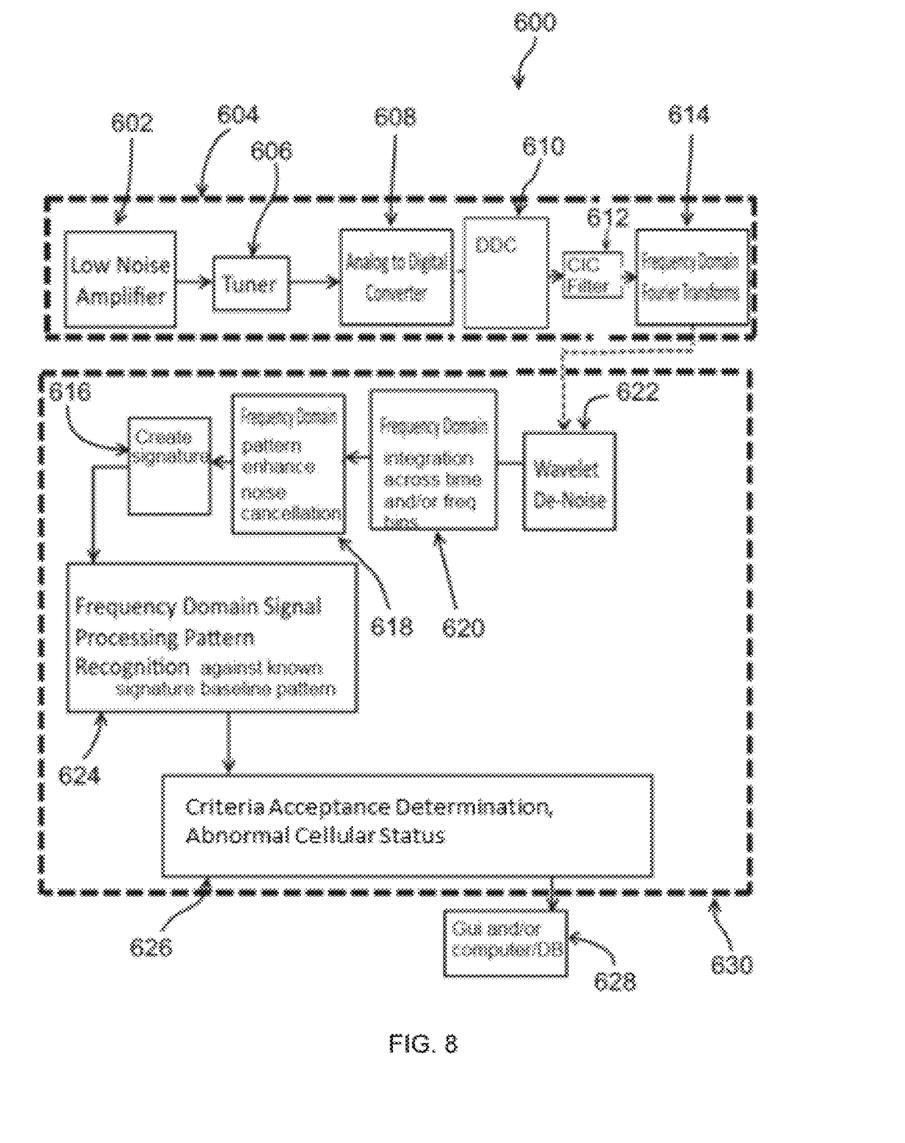
FIG. 8 is block diagram of another embodiment.

Another embodiment is shown in FIG. 8. In this embodiment 600 as in FIG. 7 a sensitive detector 604 has an LNA 602 is connected to a tuner 606. The tuner outputs a signal to an ADC 608. The digital signal is down converted by a Digital Down Converter (DDC) 610. The down converted signal is received by a frequency domain Fourier Transform (FT) device 614. The FT takes a signal in the time domain and converts it into the frequency domain.

The biologic property measurement device 630 receives the signals from the sensitive detector and applies wavelet denoising 622. It then integrates the time or frequency bins. The frequency domain pattern is enhanced with noise cancelation 618 and a signature is created 616. The frequency domain signal processing pattern recognition 624 is performed against a known signature base line pattern. A threshold is applied against the processed signal to determine whether the sample status is abnormal.

The apparatus has at least one logic circuit to combine a plurality of signals received from an array of a plurality of antennas. The combining of signals and windowing the signals creates of more coherent signal suitable for analysis.

Figure 9:
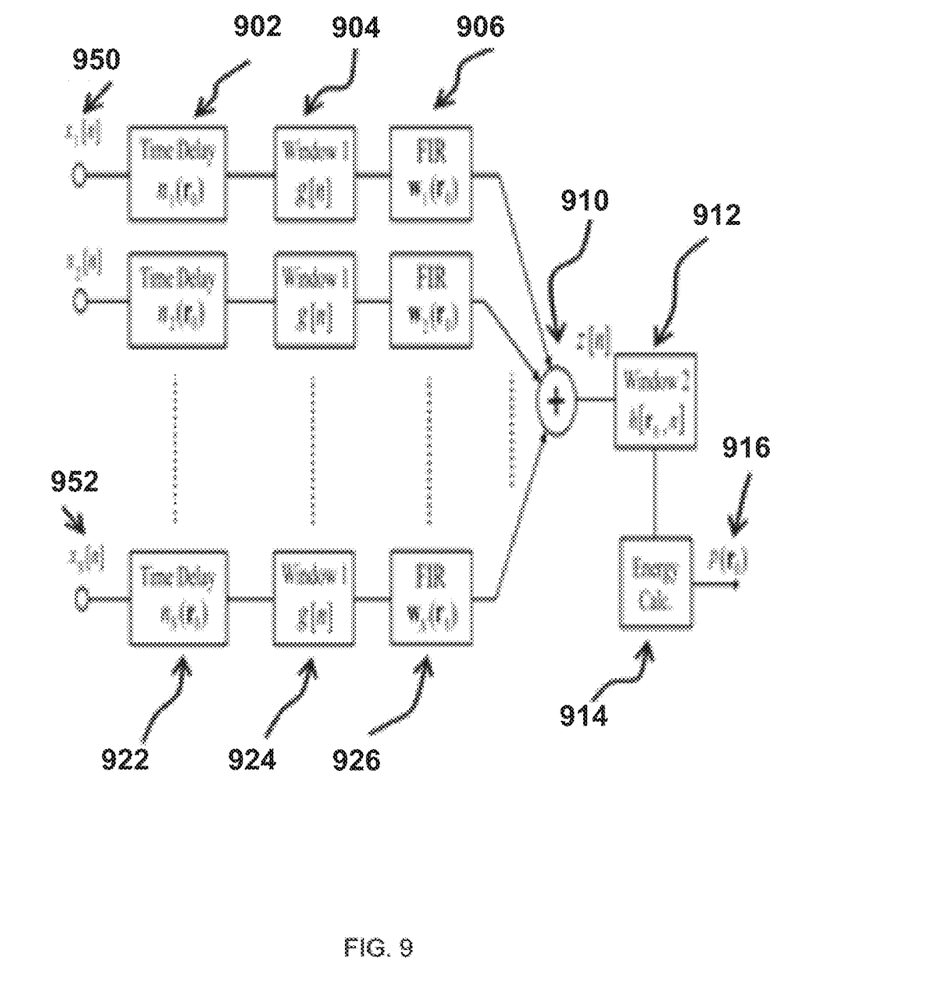
FIG. 9 is illustrative diagram of the sampling of a plurality of signals in the operation of the device.

FIG. 9 is illustrative diagram of the sampling of a plurality of signals in the operation of the device. Each non-distorted signal, x1 550 through xN 552 is combined 510 through synchronizing the signals with their independent time delays based on positions 502-522, applying a windowing function 504-524 and then Finite Impulse Response filter 506-526. The resulting signal 512 is further windowed to remove cluttered signal and the energy 514 is calculated from the resulting windowed signal 512. The purpose of this is to remove noise from the measurements, as well as removing the strongest influence of the reflected signals, typically from the surface boundary. This is required to acquire the most sensitive signals from the internal structure.

Figure 10:
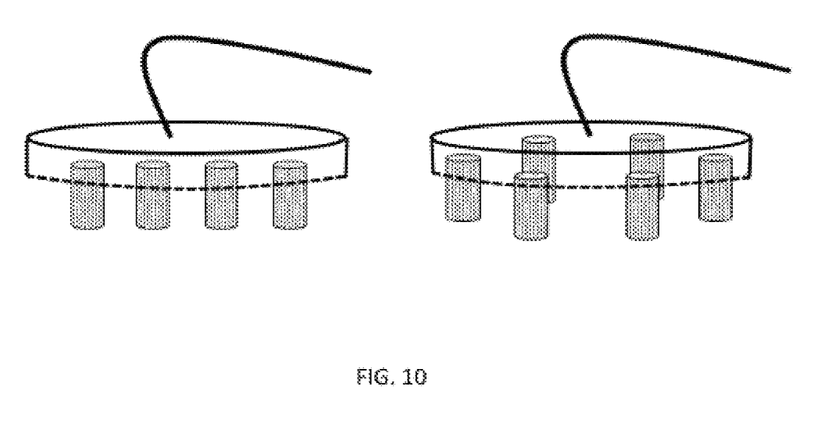
FIG. 10 shows an alternate embodiment of an array of probes in a linear arrangement and a polygonal arrangement.

FIG. 10 shows an alternate embodiment of an array of probes in a linear arrangement and a polygonal arrangement.

The presently preferred embodiment of the device is benchtop system as shown. It can be configured to assess 3D cell cultures, tissue samples and proteins.

Another embodiment would be to have the apparatus continuously monitoring cell cultures in an industrial setting.

Another embodiment would be to have the apparatus monitoring food for the presence of contamination by bacteria.

Another embodiment of the device is configured to monitor existing cell culture incubators to provide real-time assessment of cellular health.

What is claimed is:

1. An apparatus, comprising:
   a far field antenna array comprising antennas configured to be inserted into an interior of a cell, containing a biological cell culture, through an open end of the cell;
   a dielectric probe configured to be positioned external to the cell; and
   a radio frequency (RF) detector connectable to said far field antenna array and said dielectric probe.

2. The apparatus of claim 1, wherein said dielectric probe comprises a near field transmitting probe.

3. The apparatus of claim 1, wherein said dielectric probe comprises two dielectric probes disposed concentric with each other, one dielectric probe from said two dielectric probes connectable to said RF detector and another dielectric probe connectable to an RF power supply.

4. An apparatus, comprising:
   a cell comprising an open end and a closed end, the cell configured to receive a sample of a biological culture within a hollow interior between open and closed ends;
   an antenna array comprising antennas configured to be inserted into the hollow interior through the open end;
   a dielectric probe configured to be positioned external to the cell;
   a radio frequency (RF) detector configured to receive signals from the antenna array and from the dielectric probe; and
   a controller.

5. The apparatus of claim 1, wherein the dielectric probe configured to be positioned at a closed end of the cell, at a distance from the antenna array.

6. The apparatus of claim 4, wherein said dielectric probe comprises two dielectric probes disposed at a distance from each other across the biological cell culture, one dielectric probe from said two dielectric probes connectable to said RF detector and the other dielectric probe from said two dielectric probes connectable to an RF power supply.

7. The apparatus of claim 4, wherein the controller configured to receive and process a measurement of a dielectric response versus frequency from the dielectric probe and a measurement of a far field propagation and reflection across an ultra-wide bandwidth from the antenna array.

8. The apparatus of claim 4, wherein the dielectric probe configured to be positioned at the closed end of the cell, at a distance from the antenna array and across the biological culture.

9. The apparatus of claim 4, wherein the controller configured to:
   combine digital signals acquired at the antenna array and the dielectric probe and received from the RF detector through synchronizing digital signals with their independent time delays based on positions;
   apply a windowing function on combined digitals signals;
   apply a finite impulse response filter; and
   window a resulting signal from the finite impulse response filter; and
   calculate energy from windowed resulting signal.

10. The apparatus of claim 4, wherein the controller configured to compare a spectra and permittivity of the sample to a spectra of healthy cell cultures with an artificial neural network trained to classify signals received at the RF detector.

11. The apparatus of claim 4, wherein the controller configured to compare a spectra and permittivity of the sample to healthy cell cultures with a Multilayer Perceptron (MLP) feed forward neural network trained with Back Propagation (BP) to classify received signals from the RF detector.

12. An apparatus, comprising:
    a cell comprising an open end and a closed end, the cell configured to receive a sample of a biological culture within a hollow interior between open and closed ends;

an antenna array comprising antennas configured to be inserted into the hollow interior through the open end;

a dielectric probe configured to be positioned at the closed end of the cell, at a distance from the antenna array;

a radio frequency (RF) detector configured to receive signals from the antenna array and from the dielectric probe; and a biological property measurement device.

13. The apparatus of claim 11, wherein the RF detector comprises:

a low noise amplifier;

an analog to digital converter;

a digital down converter; and a device to convert a signal from the digital down converter from a time domain into a frequency domain;

the RF detector configured to amplify, tune and convert each signal acquired at the antenna array and the dielectric probe into a digital signal.

14. The apparatus of claim 13, wherein the biological property measurement device configured to:

receive the signals from the RF detector;

apply wavelet denoising to received signals;

cancel noise from received signals;

create a signature of the received signals; and compare the signature against a signature baseline pattern.

15. The apparatus of claim 14, wherein the biological property measurement device configured to apply threshold and to determine a status of the sample represents an abnormal status as compared with a sample of a healthy biological culture.

* * * * *